United States Patent
Maruyama (10) Patent No.: US 7,794,392 B2
(45) Date of Patent: Sep. 14, 2010

(54) BENT STATE HOLDING MECHANISM OF AN ENDOSCOPE

(75) Inventor: Yoshinori Maruyama, Saitama (JP)

(73) Assignee: Hoya Corporation, Tokyo (JP)

( * ) Notice: Subject to any disclaimer, the term of this patent is extended or adjusted under 35 U.S.C. 154(b) by 759 days.

(21) Appl. No.: 11/737,331

(22) Filed: Apr. 19, 2007

(65) Prior Publication Data

US 2007/0255103 A1 Nov. 1, 2007

(30) Foreign Application Priority Data

Apr. 26, 2006 (JP) ............................. 2006-121598

(51) Int. Cl.
*A61B 1/00* (2006.01)
(52) U.S. Cl. .................... 600/148; 600/146; 600/147
(58) Field of Classification Search ......... 600/143–149, 600/118, 131
See application file for complete search history.

(56) References Cited

FOREIGN PATENT DOCUMENTS

| JP | 9-098942 | 4/1997 |
| JP | 10-286220 | 10/1998 |
| JP | 2000166861 A * | 6/2000 |
| JP | 2005-160791 | 6/2005 |

OTHER PUBLICATIONS

English Language Abstract and English Language Computer-Generated Translation of JP 10-286220.
English Language Abstract and English Language Computer-Generated Translation of JP 9-098942.
English Language Abstract and English Language Computer-Generated Translation of JP 2005-160791.
U.S. Appl. No. 11/737,291 to Maruyama, filed Apr. 19, 2007.

* cited by examiner

*Primary Examiner*—Linda C Dvorak
*Assistant Examiner*—Ryan Henderson
(74) *Attorney, Agent, or Firm*—Greenblum & Bernstein P.L.C.

(57) ABSTRACT

A bent state holding mechanism of an endoscope including a bending mechanism having a rotatable bending member, includes a bent state holding member for switching between a bent-state holding state and a bendable-portion free state; and a click mechanism for providing a tactile feel to the bent state holding member when rotated to the bent-state holding state and/or when rotated to the bendable-portion free state. The click mechanism includes a click leaf spring having a protrusion formed therein, and a click projection projecting toward a surface of the click leaf spring, one of the click leaf spring and the click projection being configured to rotate together with the bent state holding member upon rotation thereof. Rotating the bent state holding member causes the click projection to abut against the protrusion and ride over the protrusion with a click action while resiliently deforming the click leaf spring.

6 Claims, 11 Drawing Sheets

PRIOR ART

BENT STATE HOLDING MECHANISM OF AN ENDOSCOPE

BACKGROUND OF THE INVENTION

1. Field of the Invention

The present invention relates to a bent state holding mechanism of an endoscope.

2. Description of the Related Art

In typical endoscopes, a bendable portion control mechanism (bending mechanism) for bending a bendable portion, which is provided in the vicinity of the distal end of an insertion portion of the endoscope, by remote control is freely rotatably mounted to the control portion that is coupled to the proximal end of the insertion portion of the endoscope. Such endoscopes are provided with a bent state holding mechanism for freely switching between a bent-state holding state, where frictional resistance is exerted on the rotating operation of the bending mechanism so that the free end of the insertion portion of the endoscope remains directed toward a target affected area or the like, and a bendable-portion free state where no frictional resistance is exerted on the rotating operation of the bending mechanism, by manually rotating a bent state holding knob.

Additionally, conventional endoscopes provided with click members (tactile-response members) which provide a tactile "click" feel to the rotating operation of the bent state holding knob so that the operator of the endoscope can feel a change in state of the bent state holding knob with his/her hand when the bent state holding knob is operated to move to the aforementioned bent-state holding state and/or when the bent state holding knob is operated to move to the aforementioned bendable-portion free state (for instance, this type of endoscope is disclosed in Japanese unexamined patent publication H10-286220).

Figure 13:
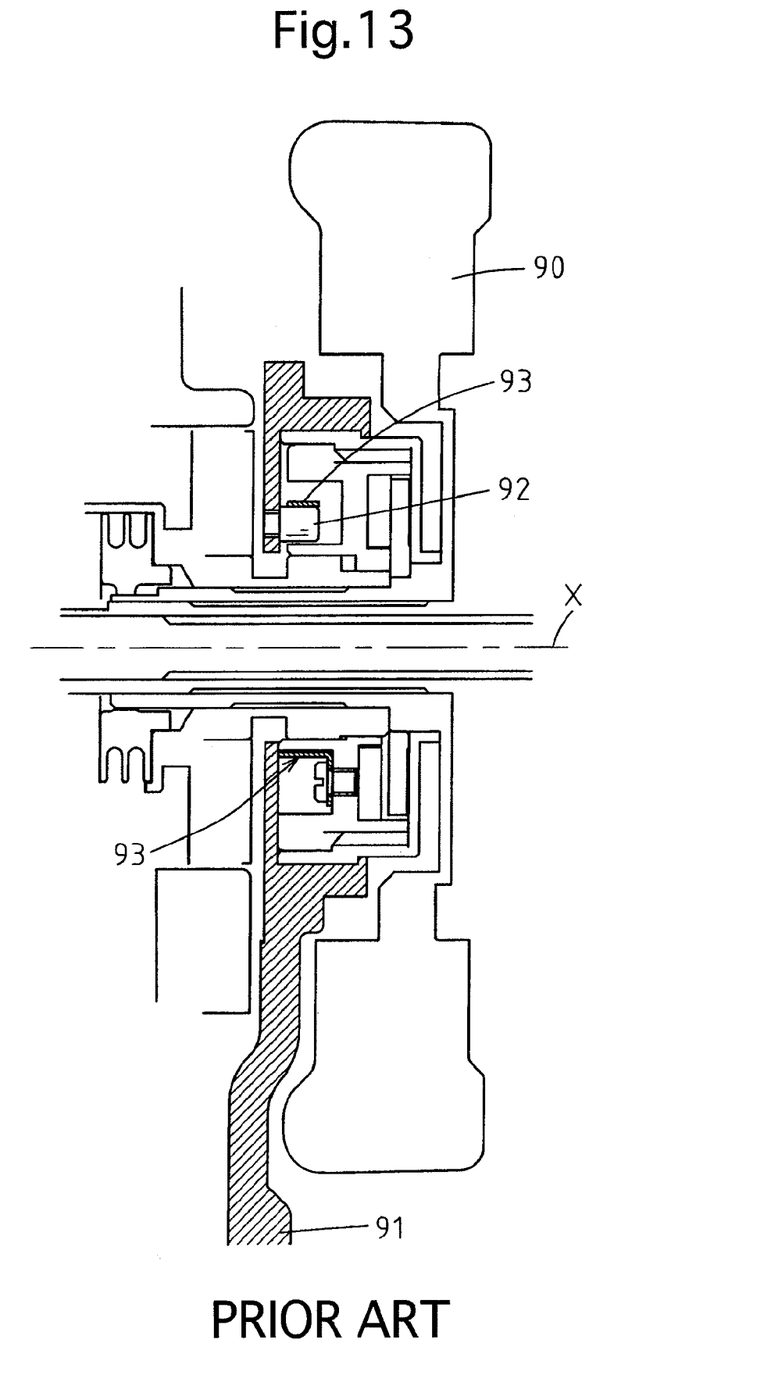
FIG. 13 is a cross sectional view of a bent state holding mechanism of a conventional endoscope.

FIG. 13 shows a bent state holding mechanism of a conventional endoscope like the aforementioned conventional endoscope. This bent state holding mechanism is provided with a bent state holding knob 91 which is operated to switch between a bent-state holding state, in which frictional resistance is exerted on the rotating operation of the bending mechanism to hold a bendable portion control knob 90, which is mounted to the control portion of the endoscope to be freely rotatable about an axis X, at any given rotation position, and a bendable-portion free state in which no frictional resistance is exerted on the rotating operation of the bending mechanism. The bent state holding knob 91 is mounted to the control portion of the endoscope to be freely rotatable about the axis X.

The bent state holding mechanism is further provided with a click pin 92 and a click leaf spring 93 that are provided as click members which provide a tactile "click" feel to the rotating operation of the bent state holding knob 91 at a predetermined point in the range of rotation of the bent state holding knob 91. The click pin 92 rotates with the bent state holding knob 91 when the bent state holding knob 91 is operated to rotate, and the click leaf spring 93 is fixed to a fixing portion of the control portion to be pressed against the click pin 92 when the click pin 92 rotates.

However, as shown in FIG. 13, in the bent state holding mechanism of the conventional endoscope, the click leaf spring 93 is formed in the shape of a part of a tube surrounding the axis X so that a side of the click pin 92 is pressed against a surface of the click leaf spring 93.

Due to this structure, the thickness of the bent state holding mechanism of the conventional endoscope is great in the direction of the axis X. Accordingly, if the bent state holding mechanism is installed in an internal space of the bent state holding knob, the bent state holding knob becomes large in size and the operability thereof deteriorates. Additionally, it becomes difficult for another mechanism (e.g., a safety torque limiting mechanism for the case of an excessive force over a predetermined torque being exerted on the bendable portion control knob) to be installed in an internal space of the bendable portion control knob if so desired.

SUMMARY OF THE INVENTION

The present invention provides a bent state holding mechanism of an endoscope with high functionality which can be made small in thickness and size, thus making it possible to improve the operability of the endoscope by miniaturization of the bendable portion control knob and to install another mechanism in an internal space of the bendable portion control knob.

According to an aspect of the present invention, a bent state holding mechanism of an endoscope is provided, including a bending mechanism which has a rotatable bending member to bend a bendable portion of an insertion portion of the endoscope, including a bent state holding member for switching between a bent-state holding state, in which a frictional resistance is exerted on the bending mechanism to hold the bendable portion in a current position, and a bendable-portion free state, in which no frictional resistance is exerted on the bending mechanism, and a click mechanism for providing a tactile feel to the rotating operation of the bent state holding member at least one of when the bent state holding member moves to the bent-state holding state and when the bent state holding member moves to the bendable-portion free state. The click mechanism includes a click leaf spring formed so that a direction of thickness thereof corresponds to a direction of an axis of rotation of the bent state holding member and shaped into an arc-shaped ring with a center thereof on the axis of rotation of the bent state holding member, at least one protrusion being formed in the click leaf spring in the direction of thickness of the click leaf spring; and at least one click projection which projects toward a surface of the click leaf spring, one of the click leaf spring and the click projection being configured to rotate together with the bent state holding member upon rotation thereof and the other thereof being fixed so that relative movement between the click leaf spring and the click projection can occur, wherein rotating the bent state holding member causes the click projection to abut against the protrusion and thereafter ride over the protrusion with a click action while resiliently deforming the click leaf spring.

It is desirable for the click leaf spring to be formed as a substantially C-shaped ring, the protrusion of the click leaf spring being made in a vicinity of an opening of the C-shaped click leaf spring.

It is desirable for the click projections to abut against the protrusions and subsequently ride over the protrusions simultaneously, respectively, via the rotating of the bent state holding knob.

It is desirable for the click projections to abut against an adjacent one of the protrusions and subsequently ride over the adjacent protrusion at different positions within the range of rotation of the bent state holding knob, via the rotating of the bent state holding knob.

It is desirable for the axis of rotation of the bent state holding knob to correspond with an axis of rotation of the bending mechanism.

It is desirable for two of the protrusions to be formed in a vicinity of circumferentially-opposed ends of the C-shaped click leaf spring, respectively.

It is desirable for a middle portion of the C-shaped click leaf spring in a circumferential direction thereof to be fixed relative to the control portion so that portions of the C-shaped click leaf spring on opposite sides of the middle portion can be resiliently deformed independently of each other in the direction of thickness of the click leaf spring.

It is desirable for the middle portion of the C-shaped click leaf spring in a circumferential direction thereof to be fixed relative to the control portion by at least one set-screw, a head of which also serves as a stop pin for determining the range of rotation of the bent state holding knob relative to the control portion.

It is desirable for the protrusions to be arranged at equi-angular intervals in an arc shape to face the surface of the click leaf spring.

According to the present invention, since the click mechanism for providing a tactile feel to the rotating operation of the bent state holding knob is composed of a click leaf spring and at least one click projection, wherein the click leaf spring is formed so that the direction of thickness thereof corresponds to the direction of the axis of rotation of the bent state holding knob and wherein the click projection is formed to project toward a surface of said click leaf spring, the operability of the endoscope can be improved by miniaturization of the bendable portion control knob and another mechanism can be installed in an internal space of the bendable portion control knob. Accordingly, a bent state holding mechanism of an endoscope with high functionality is achieved.

The present disclosure relates to subject matter contained in Japanese Patent Application No. 2006-121598 (filed on Apr. 26, 2006) which is expressly incorporated herein in its entirety.

BRIEF DESCRIPTION OF THE DRAWINGS

The present invention will be described below in detail with reference to the accompanying drawings in which.

DESCRIPTION OF THE PREFERRED EMBODIMENTS

Figure 2:
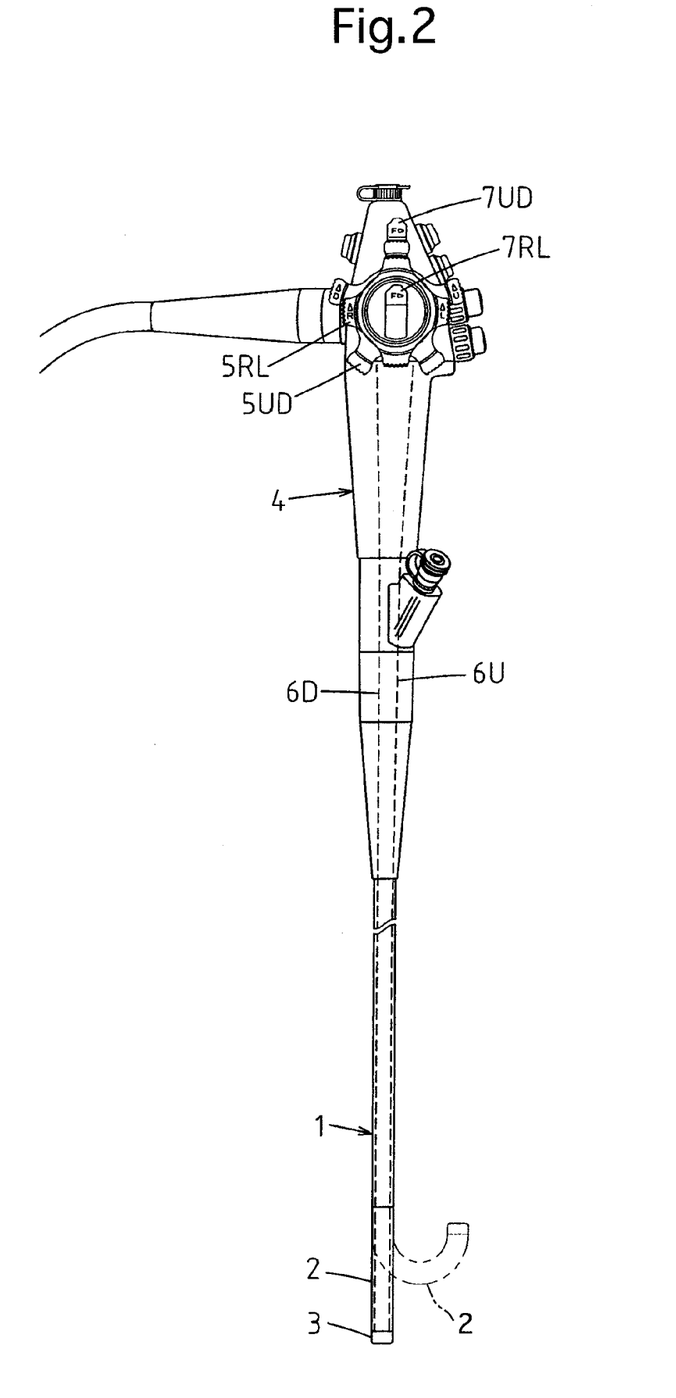
FIG. 2 is an external view of the endoscope, showing the overall structure thereof.

FIG. 2 shows the general configuration of a first embodiment of the endoscope. The endoscope is provided with a flexible insertion portion 1 and a control portion 4 coupled to the proximal end of the insertion portion 1. The insertion portion 1 is provided in the vicinity of the distal end (free end) thereof with a remote-controllable bendable portion 2, and is further provided with an end body 3 fixed to the end (free end) of the bendable portion 2. An objective window and others (not shown) are provided in the end body 3.

The control portion 4, which is coupled to the proximal end of the insertion portion 1, is provided thereon with a U-D control knob 5UD for bending the bendable portion 2 upward and downward and an R-L control knob 5RL for bending the bendable portion 2 rightward and leftward. The U-D control knob 5UD and the R-L control knob 5RL are overlaid on each other and coaxially arranged so that each of the U-D control knob 5UD and the R-L control knob 5RL can be freely rotated on a common axis.

An upward-direction control wire 6U and a downward-direction control wire 6D are inserted into the insertion portion 1 and distal ends thereof and are fixed to the end body 3. Turning the U-D control knob 5UD counterclockwise causes the upward-direction control wire 6U to be pulled toward the control portion 4 to thereby cause the bendable portion 2 to bend upward (e.g., upward direction of a monitoring screen which corresponds to forward direction of the control portion 4) as shown by two-dot chain lines in FIG. 2. Turning the U-D control knob 5UD clockwise causes the downward-direction control wire 6D to be pulled toward the control portion 4 to thereby cause the bendable portion 2 to bend downward. The distal ends of the upward-direction control wire 6U and the downward-direction control wire 6D are fixed to the end body 3.

Additionally, turning the R-L control knob 5RL counterclockwise causes a leftward-direction control wire 6L, which is inserted into the insertion portion 1 to be installed therein, to be pulled toward the control portion 4 to thereby cause the bendable portion 2 to bend leftward. Turning the R-L control knob 5RL clockwise causes a rightward-direction control wire 6R, which is installed in the insertion portion 1, to be pulled toward the control portion 4 to thereby cause the bendable portion 2 to bend rightward. In this manner, the bendable portion 2 can be remote-controlled to be bent freely in any directions at any angle from the control portion 4 side.

The control portion 4 is provided with a U-D bent state holding knob 7UD which is operated to hold the U-D control knob 5UD at any given rotation position and a R-L bent state holding knob 7RL which is operated to hold the R-L control knob 5RL at any given rotation position. The U-D bent state holding knob 7UD and the R-L bent state holding knob 7RL are arranged to be capable of being operated to rotate coaxially with the U-D control knob 5UD and the R-L control knob 5RL.

Figure 3:
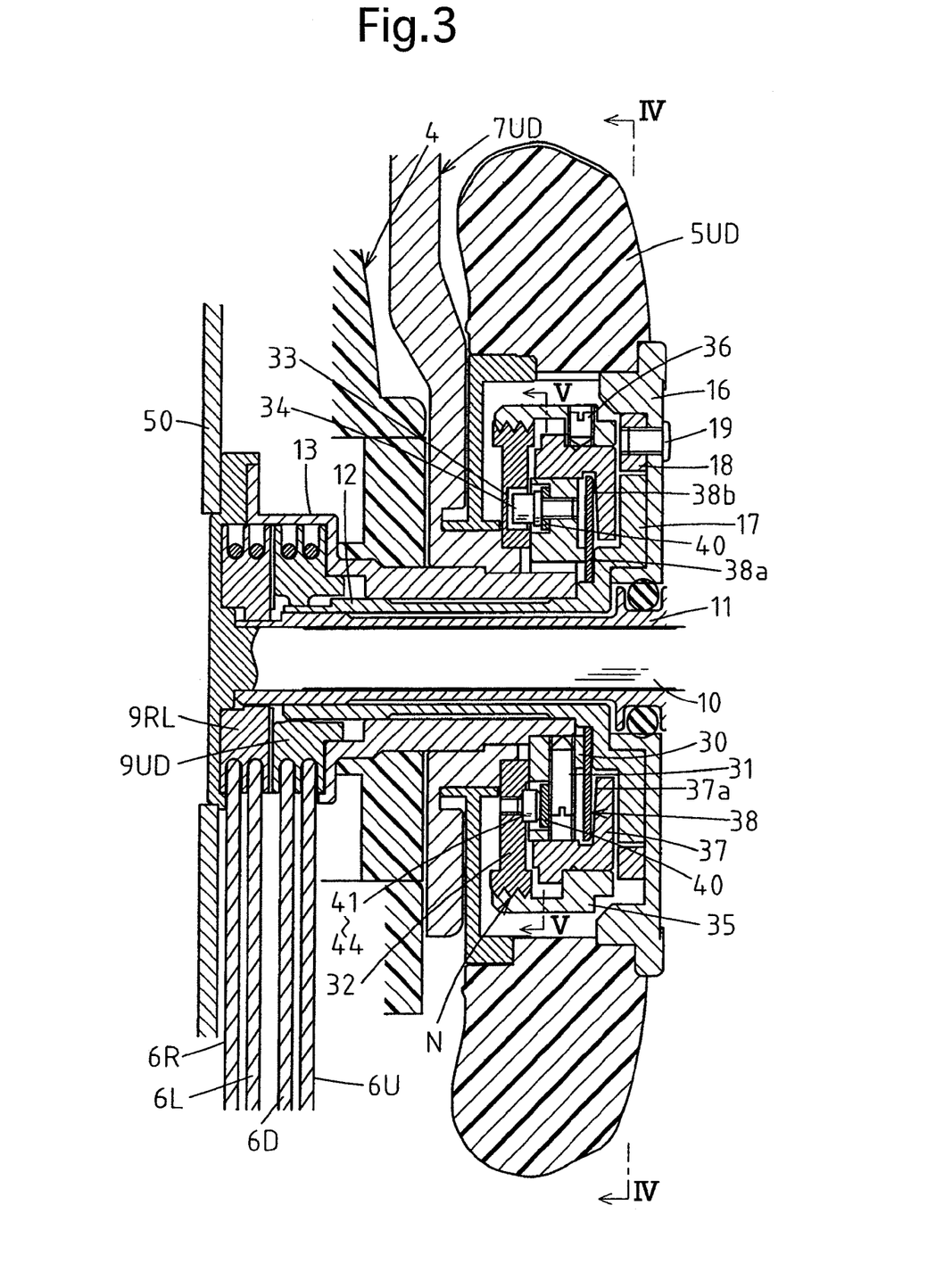
FIG. 3 is a cross sectional view of a bendable portion U-D control mechanism of the endoscope in a bendable-portion free state thereof.

FIG. 3 shows a bendable portion U-D control mechanism, installed to the control portion 4 in a freely rotatable manner, for bending the bendable portion 2 vertically. The U-D control knob 5UD is formed so that a ring-shaped control portion thereof has a large internal space, and a supporting column (cylindrical shaft) 10 of the operating force transmission mechanism is fixed to an internal main frame 50 of the control portion 4 to extend upright coaxially with the axis of the U-D control knob 5UD.

As shown in FIG. 3, the operating force transmission mechanism is provided with a U-D pulley having two outer peripheral grooves in which the upward-direction control wire 6U and the downward-direction control wire 6D are engaged and wound around the U-D pulley 9UD by a half to one turn and extend therefrom toward the bendable portion 2. The operating force transmission mechanism is also provided with an R-L pulley 9RL similar in structure to the U-D pulley 9UD, having two outer peripheral grooves in which the leftward-direction control wire 6L and the rightward-direction control wire 6R are engaged to be wound around the R-L pulley 9RL by a half to one turn and extend therefrom toward the bendable portion 2.

An R-L tubular drive shaft 11 fixed at one end thereof to the R-L pulley 9RL is rotatably fitted on the supporting column 10 and a U-D tubular drive shaft 12 fixed at one end thereof to the U-D pulley 9UD is rotatably fitted on the R-L tubular drive shaft 11. In order to transmit rotations of the R-L control knob 5RL and the U-D control knob 5UD to the R-L pulley 9RL and the U-D pulley 9UD, the R-L tubular drive shaft 11 and the U-D tubular drive shaft 12 project outwards (upwards as viewed in FIG. 3) from the control portion 4 so that the other ends thereof are positioned outside of the control portion 4 to be associated with the R-L control knob 5RL and the U-D control knob 5UD, respectively.

A cylindrical U-D bearing 13 in which the U-D tubular drive shaft 12 is fitted to be freely rotatable on the axis thereof is fixed at the base end of the U-D bearing 13 to a base of the supporting column 10 which is fixed to the internal main frame 50 of the control portion 4. The U-D bearing 13 also serves as a pulley cover which covers the R-L pulley 9RL and the U-D pulley 9UD to prevent the control wires 6U and 6D and the control wires 6R and 6L from being disengaged from the U-D pulley 9UD and the R-L pulley 9RL, respectively.

Rotating the U-D tubular drive shaft 12 about the axis thereof (on the axis of the supporting column 10) causes the U-D pulley 9UD to rotate to thereby pull one of the control wires 6U and 6D in accordance the direction of rotation of the U-D tubular drive shaft 12. Likewise, rotating the R-L tubular drive shaft 11 about the axis thereof (on the axis of the supporting column 10) causes the R-L pulley 9RL to rotate to thereby pull one of the control wires 6R and 6L in accordance the direction of rotation of the R-L tubular drive shaft 11.

A substantially disk-shaped seating plate 16 that is integral with the U-D control knob 5UD is positioned thereon to close an outer open end of the internal space of the U-D control knob 5UD, and an outer end surface of a grooved rotational plate 17 made of metal which is formed integral with the U-D tubular drive shaft 12 is in sliding contact with an inner surface of the seating plate 16 to be freely rotatable on the axis of the grooved rotational plate 17.

Figure 4:
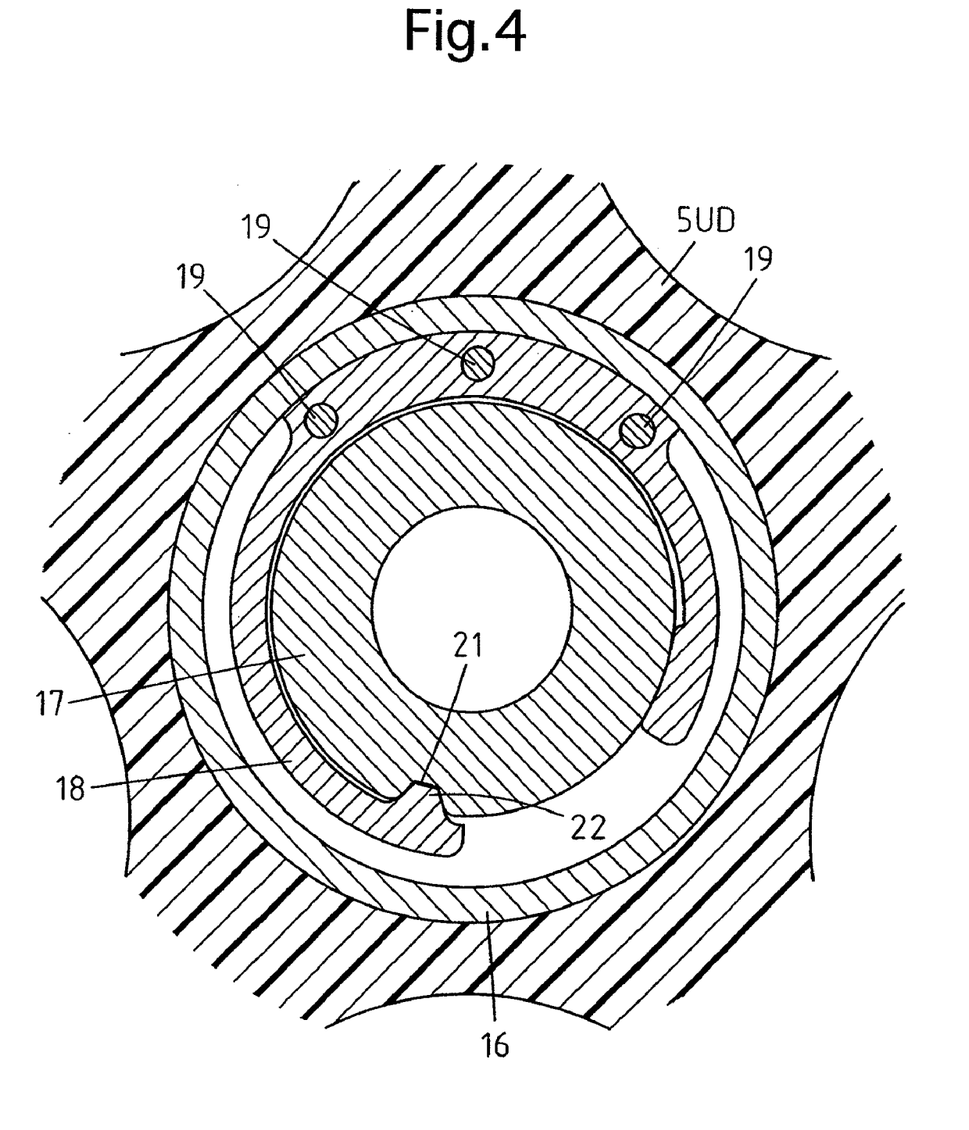
FIG. 4 is a cross sectional view of a torque limiting mechanism of the endoscope (taken along IV-IV line shown in FIG. 3)

As shown in FIG. 4 that shows a cross sectional view taken along IV-IV line in FIG. 3, the grooved rotational plate 17, the outer edge of which is formed in a circular shape as a whole, is provided on a part of an outer peripheral surface thereof with an engaging groove (notch) 21. An arc-shaped spring engaging arm 18 made of a resilient material is fixed at a base end portion thereof to the seating plate 16 by three set crews 19 to be positioned around an outer periphery of the grooved rotational plate 17. The spring engaging arm 18 is provided at a free end thereof with an engaging lug 22 which projects radially inwards to be freely capable of being engaged in and disengaged from the engaging groove 21 of the grooved rotational plate 17.

When no external force is applied to the spring engaging arm 18, the spring engaging arm 18 is set in a state shown in FIG. 4 where the engaging lug 22 is engaged in the engaging groove 21 of the grooved rotational plate 17. The spring engaging arm 18 in this state can freely rotate integrally with the seating plate 16 about the axis of the thereof, and the engaging lug 22 remains engaged in the engaging groove 21 of the grooved rotational plate 17 when a torque exerted on the U-D control knob 5UD is equal to or less than a predetermined torque.

Accordingly, when the U-D control knob 5UD is manually rotated, the spring engaging arm 18 rotates with the seating plate 16 to thereby cause the grooved rotational plate 17 to rotate, so that the rotational control force exerted on the U-D control knob 5UD is transmitted to the control wires 6U and 6D via the U-D tubular drive shaft 12 and others.

Upon an excessive control force exceeding the aforementioned predetermined torque being exerted on the U-D control knob 5UD, the spring engaging arm 18 is resiliently deformed to make the engaging lug 22 disengaged from the engaging groove 21 of the grooved rotational plate 17 so that the grooved rotational plate 17 does not rotate with the seating plate 16 even if the seating plate 16 rotates, which prevents the U-D tubular drive shaft 12 from being rotated by an operation of the U-D control knob 5UD.

In this manner, a safety torque limiting mechanism for the case where an excessive force exceeding the predetermined torque is exerted on the U-D control knob 5UD includes the grooved rotational plate 17, the spring engaging arm 18, the engaging groove 21, the engaging lug 22, and is installed in an internal space of the U-D control knob 5UD.

Reference numerals 30 through 38 shown in FIG. 3 designate elements of a U-D bent state holding mechanism which exerts frictional resistance on the rotating operation of the bendable portion U-D control mechanism to hold the bendable portion U-D control mechanism (which includes the U-D control knob 5UD, the U-D tubular drive shaft 12 connected to the U-D control knob 5UD, and the U-D pulley 9UD) at any given rotation position. The U-D bent state holding mechanism is accommodated and arranged in an internal space of the U-D control knob 5UD and can operate to exert friction on the rotating operation of the bendable portion U-D control mechanism and to stop exerting the same thereon.

An immovable base 30, a substantially square shaft portion of which is engaged in a corresponding substantially square hole of the metal disk 37, is secured to the cylindrical U-D bearing 13 (fixed to the main frame 50) in the vicinity of the top end thereof by set screws 31. The U-D bent state holding knob 7UD is fitted on an outer peripheral surface of the U-D bearing 13 to be freely rotatable thereon. A male screw ring 32 having a male screw thread on an outer peripheral surface thereof is provided in a central portion thereof with a polygonal-shaped hole, and the U-D bent state holding knob 7UD is provided in a central portion thereof with a corresponding polygonal-shaped shaft portion which is firmly fitted in the polygonal-shaped hole of the male screw ring 32 so that the male screw ring 32 rotates with the U-D bent state holding knob 7UD.

The range of rotation of the U-D bent state holding knob 7UD (the male screw ring 32) is defined by an arc-shaped groove 33 which is formed in the male screw ring 32 and a stop pin 34 which projects from the immovable base 30 to be engaged in the arc-shaped groove 33.

A female screw ring 35 is screw-engaged with the male screw ring 32. A female screw thread of the female screw ring 35 which is screw-engaged with the male screw thread of the male screw ring 32 is formed on a substantially lower-half of the inner peripheral surface of the female screw ring 35. The letter "N" shown in FIG. 3 designates the portion of engagement between the female screw thread of the female screw ring 35 and the male screw thread of the male screw ring 32. A metal disk (frictional resistance producing member) 37 is positioned inside of an upper half portion of the female screw ring 35 and fixed integrally thereto by a set screw 36.

Figure 5:
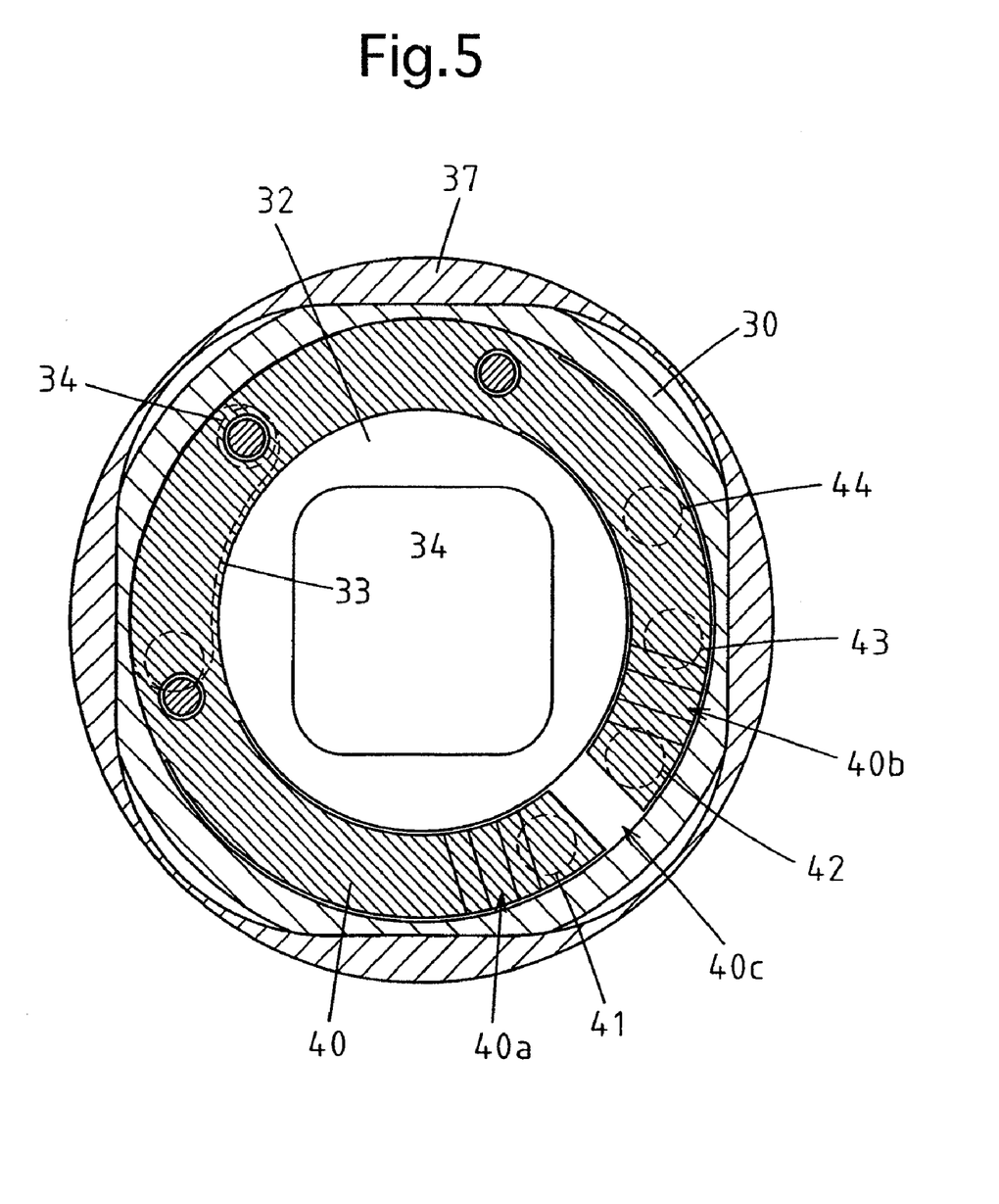
FIG. 5 is a cross sectional view of the bent state holding mechanism of the endoscope (taken along V-V line shown in FIG. 3)

The metal disk 37 is made of, e.g., brass, stainless steel or the like. As shown in FIG. 5 that shows a cross sectional view taken along V-V line in FIG. 3, the metal disk 37 has a substantially square central hole, and an inner peripheral surface of the metal disk 37 is partly engaged in an outer peripheral surface of the immovable base 30 at substantially equiangular intervals of 90 degrees in a manner to allow the metal disk 37 to move in the axial direction relative to the immovable base 30 while preventing the metal disk 37 from rotating about the axis thereof relative to the immovable base 30. Therefore, the female screw ring 35, which moves with the metal disk 37, is also freely movable in the axial direction though not rotatable about the axis of the female screw ring 35.

Figure 6:
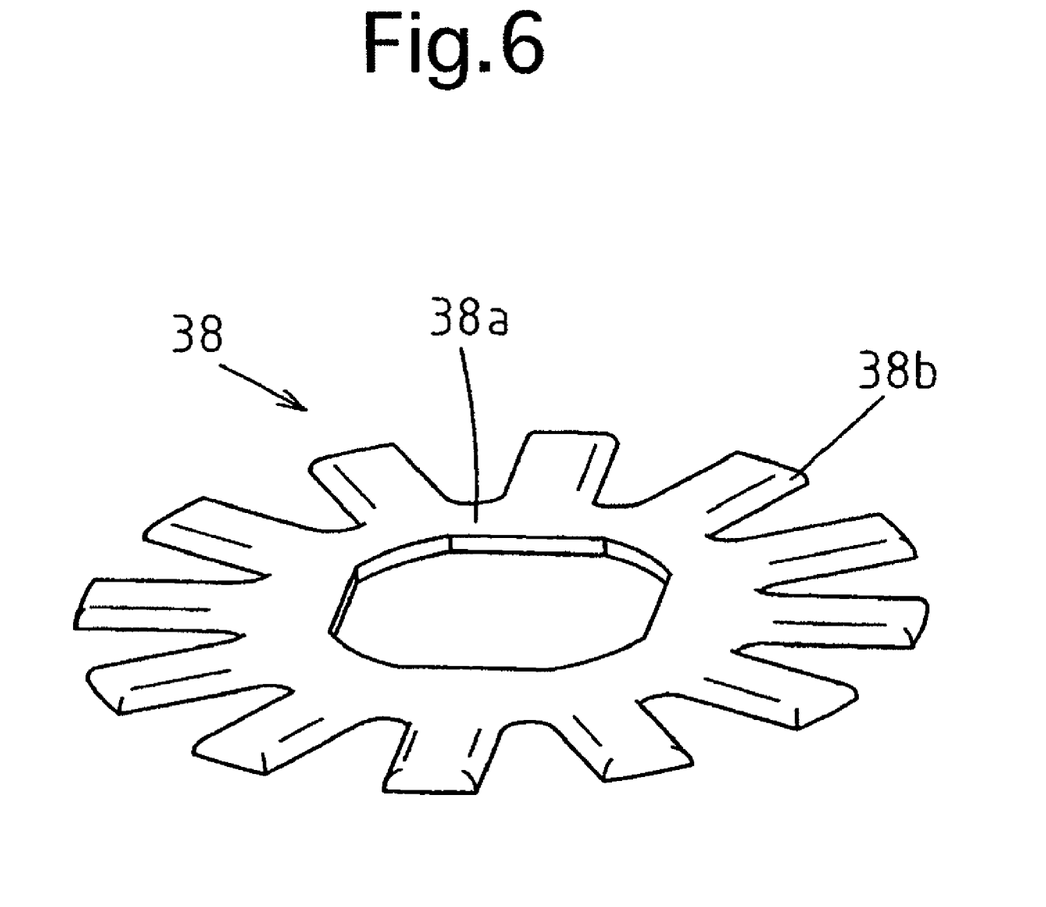
FIG. 6 is a perspective view of a friction plate spring provided as an element of the bent state holding mechanism of the endoscope.

Reference numeral 38 shown in FIGS. 3 and 6 designates a friction plate spring made of a resilient metal plate such as a spring stainless steel. The friction plate spring 38 is provided with a ring portion 38a and a plurality of radial projections (radial leaf springs) 38b which are formed integral with the ring portion 38a to project radially outwards from the ring portion 38a. The friction plate spring 38 is formed in a flat shape as a whole, and the ring portion 38a is provided at a center thereof with a substantially square hole.

The friction plate spring 38 is engaged at the square hole thereof with a portion of the U-D tubular drive shaft 12 in the vicinity of the upper end thereof as shown in FIG. 3 to rotate with the U-D tubular drive shaft 12 about the axis thereof. The back of the ring portion 38a of the friction plate spring 38 is in contact with the upper end surface of the immovable base 30 to be supported thereby.

An annular surface of the metal disk 37 which is located at a position facing the plurality of radial projections 38b of the friction plate spring 38 is formed as a pressure surface 37a which is brought to be pressed obliquely against upper flat surfaces of the plurality of radial projections 38b. More specifically, the pressure surface 37a of the metal disk 37 is formed in an umbrella-like beveled shape (truncated conical shape) which approaches the plurality of radial projections 38b in radially directions from the radially inside to the radially outside of the pressure surface 37a.

With this structure, manually rotating the U-D bent state holding knob 7UD causes the male screw ring 32 to rotate with the U-D bent state holding knob 7UD about the axis of the male screw ring 32. This rotation of the male screw ring 32 causes the female screw ring 35, which is screw-engaged with the male screw ring 32 at the portion of engagement N, and the metal disk 37, which is integral with the female screw ring 35, to move in the axial direction without rotating about the axis of the supporting column 10, so that the distance between the friction plate spring 38 and the pressure surface 37a of the metal disk 37 changes.

When the U-D bent state holding knob 7UD is at one of the opposite ends (free-state end) of the range of rotation of the U-D bent state holding knob 7UD, a slight clearance is formed between the friction plate spring 38 and the pressure surface 37a of the metal disk 37 as shown in FIG. 3 so that the friction plate spring 38 and the metal disk 37 are not in sliding contact with each other. Therefore, the metal disk 37 and the friction plate spring 38 exert no frictional resistance on the rotating operation of the bending mechanism (composed of the U-D control knob 5UD, the U-D tubular drive shaft 12, the U-D direction pulley 9UD and others) for pulling the upward-direction control wire 6U and the downward-direction control wire 6D.

Figure 7:
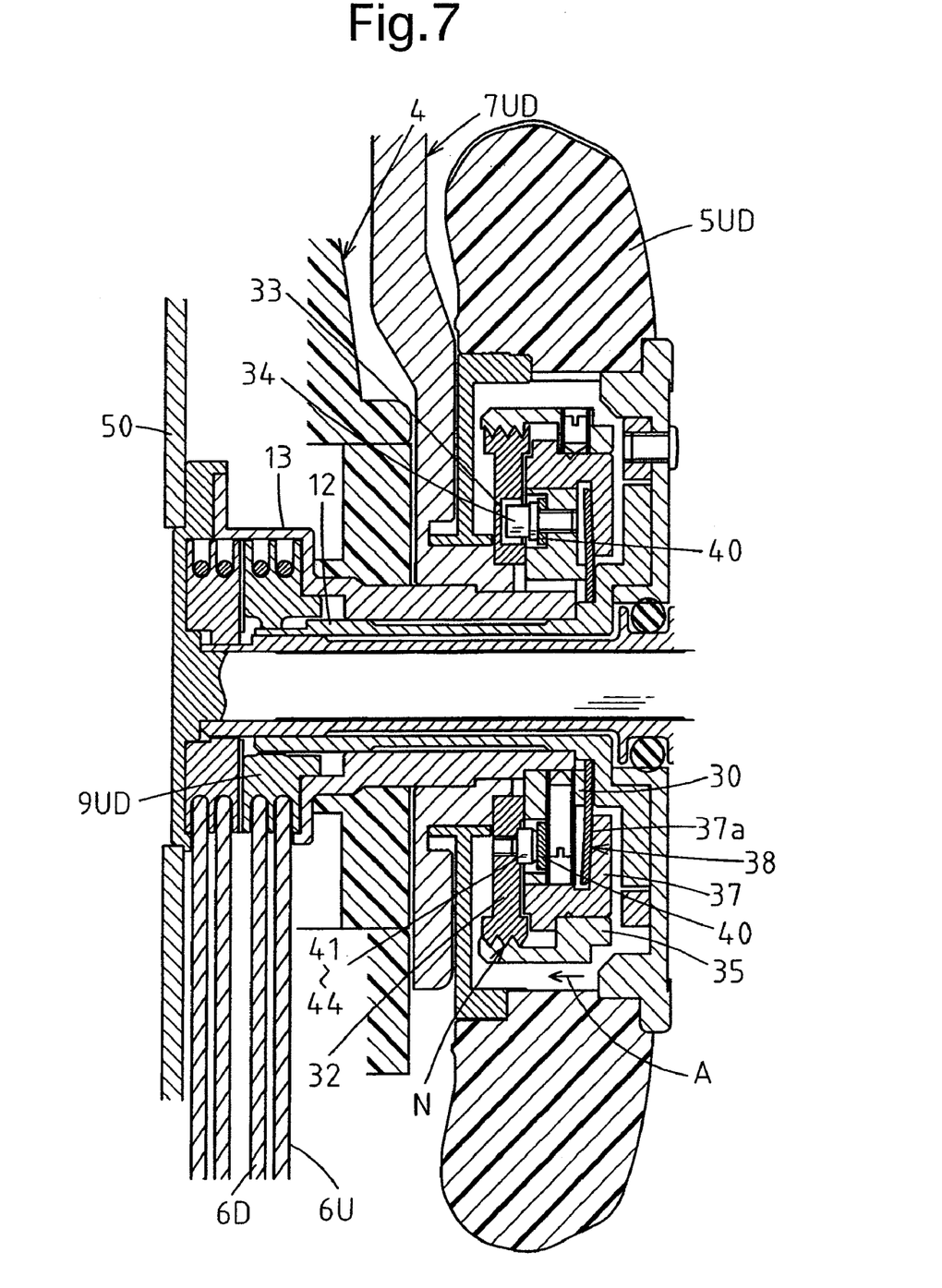
FIG. 7 is a cross sectional view of a bendable portion U-D control mechanism of the endoscope in a bent-state holding state thereof.

Rotating the U-D bent state holding knob 7UD to the other end (lock end) of the range of rotation of the U-D bent state holding knob 7UD causes the metal disk 37 to move in a direction shown by the arrow A in FIG. 7, thus causing the pressure surface 37a of the metal disk 37 to be pressed against the friction plate spring 38 so that the friction plate spring 38 and the metal disk 37 come in sliding contact with each other. Consequently, the U-D bent state holding mechanism enters a bent-state holding state in which the frictional resistance caused by this sliding contact acts on the rotating operation of the bending mechanism for pulling the upward-direction control wire 6U and the downward-direction control wire 6D.

Subsequently, rotating the U-D bent state holding knob 7UD back to the free-state position shown in FIG. 3 causes the friction plate spring 38 to return to its flat state, thus causing the U-D bent state holding mechanism to return to a bendable-portion free state in which the friction plate spring 38 is not pressed against the metal disk 37. In this manner, one can freely switch between the bent-state holding state, in which the plurality of radial projections 38b of the friction plate spring 38 and the pressure surface 37a are pressed against each other to hold the bendable portion 2 in the current state of bent thereof, and the bendable-portion free state, in which the plurality of radial projections 38b of the friction plate spring 38 and the pressure surface 37a are disengaged from each other, and between these two states one can continuously change the amount of the pressure contact between the plurality of radial projections 38b of the friction plate spring 38 and the pressure surface 37a of the metal disk 37.

Note that at least the edges of each radial projection 38b of the friction plate spring 38 which are brought to be pressed against the pressure surface 37a of the metal disk 37 are all chamfered so that each radial projection 38b can come in contact with the metal disk 37 smoothly (see FIG. 6). Moreover, since the metal disk 37 comes in sliding contact with the friction plate spring 38 from radially outermost portions of the plurality of radial projections 38b whenever the metal disk 37 is brought to be pressed against the friction plate spring 38, the magnitude of the frictional resistance which occurs by pressure contact between the friction plate spring 38 and the metal disk 37 does not change suddenly by a large amount, so that an appropriate frictional resistance is exerted on the rotating operation of the bending mechanism with stability.

As shown in FIGS. 3 and 4, the U-D bent state holding mechanism is provided with a click leaf spring 40 and four click projections (first through fourth click projections) 41 through 44. The click leaf spring 40 and the four click projections 41 through 44 serve as click members for providing a tactile "click" feel to the rotating operation of the U-D bent state holding knob 7UD upon the U-D bent state holding knob 7UD moving from the bendable-portion free state to the bent-state holding state and upon the U-D bent state holding knob 7UD moving from the bent-state holding state to the bendable-portion free state. The click leaf spring 40 is secured to the immovable base 30 by three set screws. The four click projections 41 through 44 are screw-mounted to the male screw ring 32 to be fixed thereto.

Figure 1:
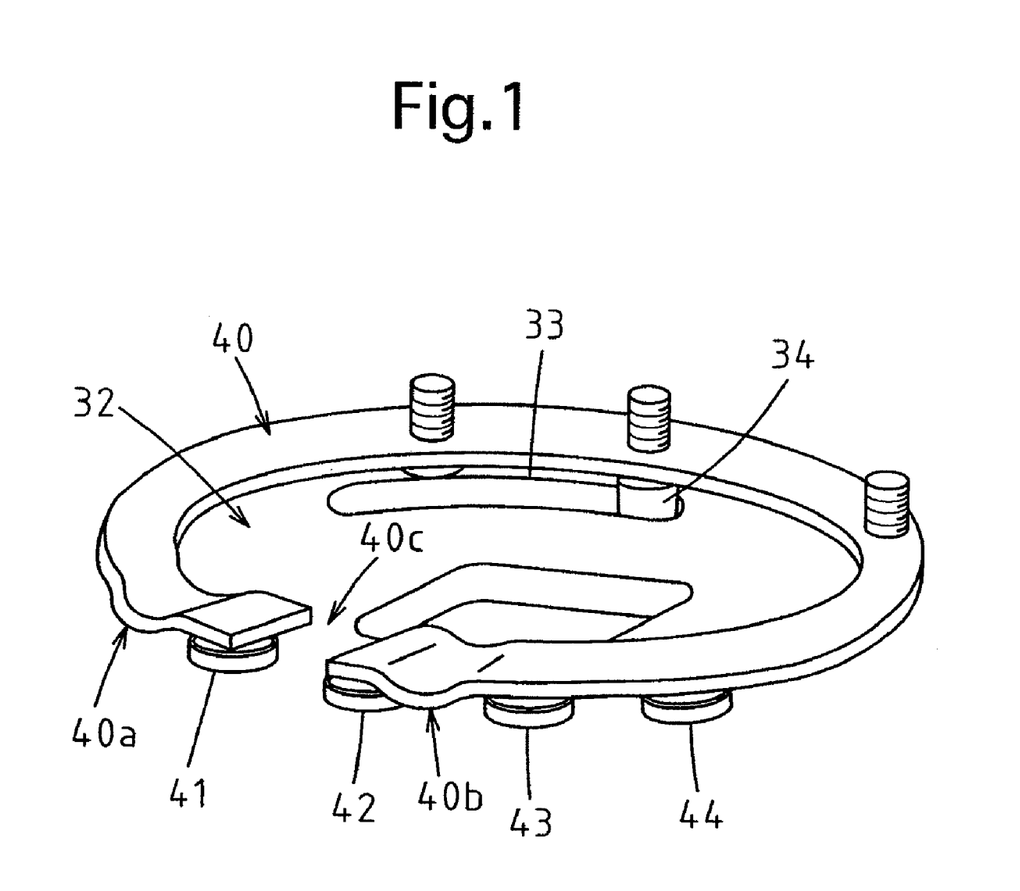
FIG. 1 is a perspective view of click members of a bent state holding mechanism and associated members in an embodiment of an endoscope according to the present invention.

FIG. 1 is a perspective view of the click leaf spring 40, the four click projections 41 through 44 and associated members, and FIG. 5 is a cross sectional view of the bent state holding mechanism of the endoscope in a state in which the U-D bent state holding knob 7UD is in the bendable-portion free state, taken along V-V line shown in FIG. 3. The click leaf spring 40 is formed so that the direction of thickness thereof corresponds to the direction of the axis of rotation of the U-D bent state holding knob 7UD and shaped into a circular-arc-shaped ring with the center thereof on the axis of rotation of the U-D bent state holding knob 7UD. Two protrusions 40a and 40b (shown as downward protrusions in FIG. 1) are formed in the click leaf spring 40 and project in the direction of thickness of the click leaf spring 40.

More specifically, the click leaf spring 40 is shaped into a substantially C-shaped ring and provided, in the vicinity of circumferentially-opposed ends of the C-shaped click leaf spring 40 on the opposite sides of a cut (opening) 40c thereof, with two protrusions (first and second protrusions) 40a and 40b, respectively, which protrude toward the male screw ring 32 (downward as viewed in FIG. 1), to which the four click projections 41 through 44 are screw-mounted. Each of the two protrusions 40a and 40b is shaped so that the surface thereof which faces the male screw ring 32 (the four click projections 41 through 44) is smoothly curved to have a smoothly-curved-arc shape. Since the click leaf spring 40 is secured to the immovable base 30 by three set screws, the click leaf spring 40 is in substantially the same state as in the case where the click leaf spring 40 is secured to the main frame 50. The stop pin 34, which determines the range of rotation of the U-D bent state holding knob 7UD (the male screw ring 32) with the arc-shaped groove 33, is made by the head of one of the aforementioned three set screws by which the click leaf spring 40 is secured to the immovable base 30.

Each of the four click projections 41 through 44 is formed in a short cylindrical column. The end surface (upper end surface as viewed in FIG. 1) of each click projection 41 through 44 is flat and the outer edge of each click projection 41 through 44 around this flat end surface thereof is smoothly chamfered. Note that the end surface of each click projection 41 through 44 can be formed as a smoothly-curved surface.

The four click projections 41 through 44 are arranged at equi-angular intervals in an arc so that all the four click projections 41 through 44 can face a surface of the click leaf spring 40. Each interval between the click projections 41 through 44 is equivalent to just half the interval between the two protrusions 40a and 40b.

Since the four click projections 41 through 44 are fixed to the male screw ring 32, the four click projections 41 through 44 rotate about the axis of rotation of the U-D control knob 5UD (i.e., the axis of rotation of the U-D bent state holding knob 7UD) while maintaining a state in which the end surfaces of the click projections 41 through 44 face a surface of the click leaf spring 40 if the U-D bent state holding knob 7UD is operated to rotate.

Figure 8:
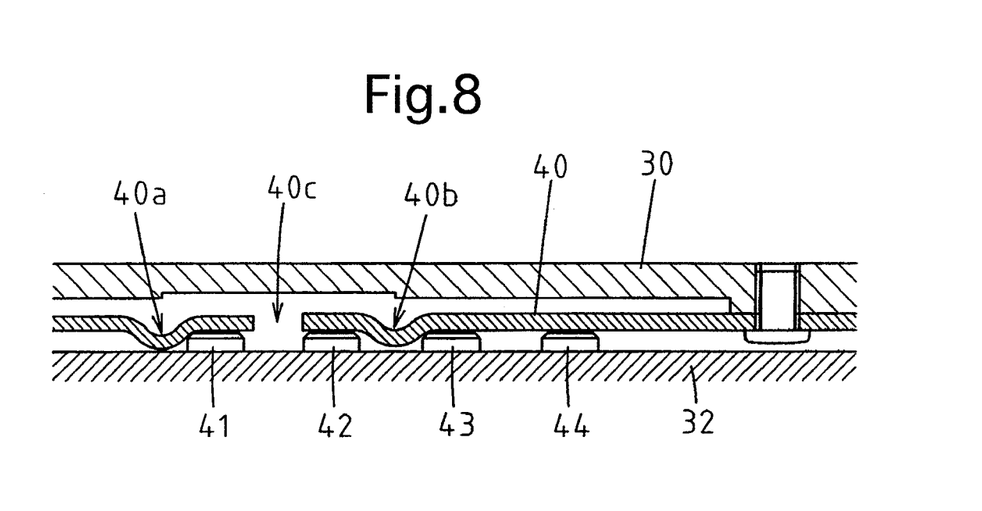
FIGS. 8 through 11 are schematic developed cross sectional views of a click leaf spring, click projections and associated members of the endoscope, showing operating status conditions of the click leaf spring and the click projections in succession.

FIG. 8 is a schematic developed cross sectional view of the click leaf spring 40, the four click projections 41 through 44 and other members associated therewith, showing a state of the click leaf spring 40 and the four click projections 41 through 44 when the U-D bent state holding knob 7UD is in the bendable-portion free state shown in FIG. 3, similar to the state shown in FIG. 5. In this state, the first click projection 41 is positioned immediately on the right side of the first protrusion 40a while the second protrusion 40b is positioned between the second and third click projections 42 and 43.

Figure 9:
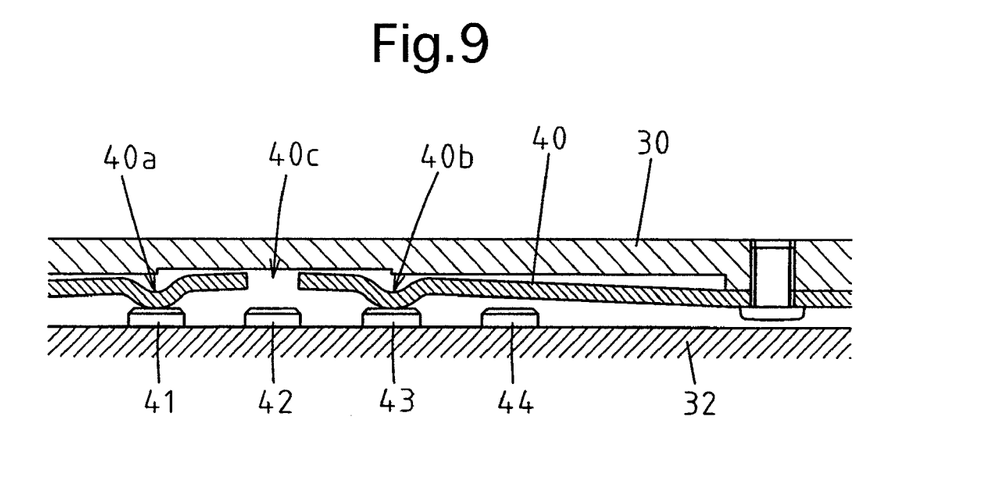
Figure 10:
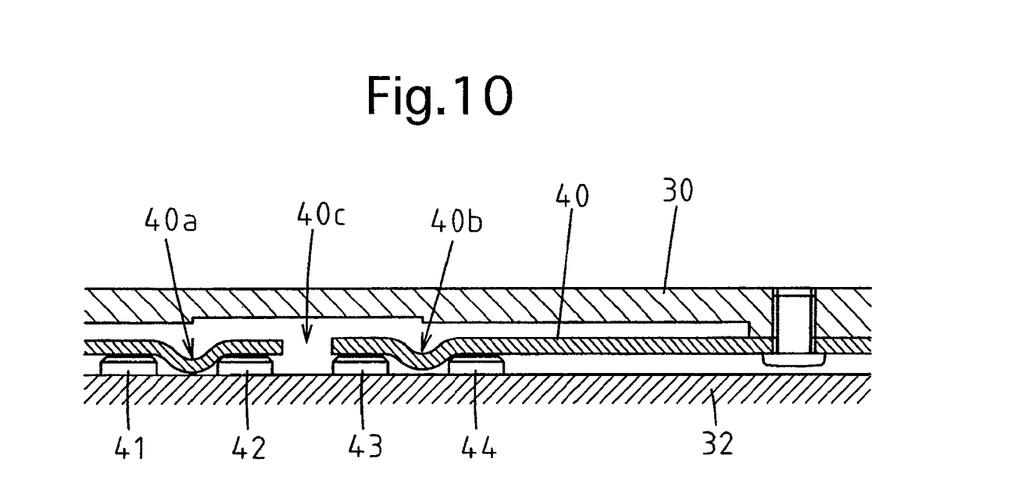
Figure 11:
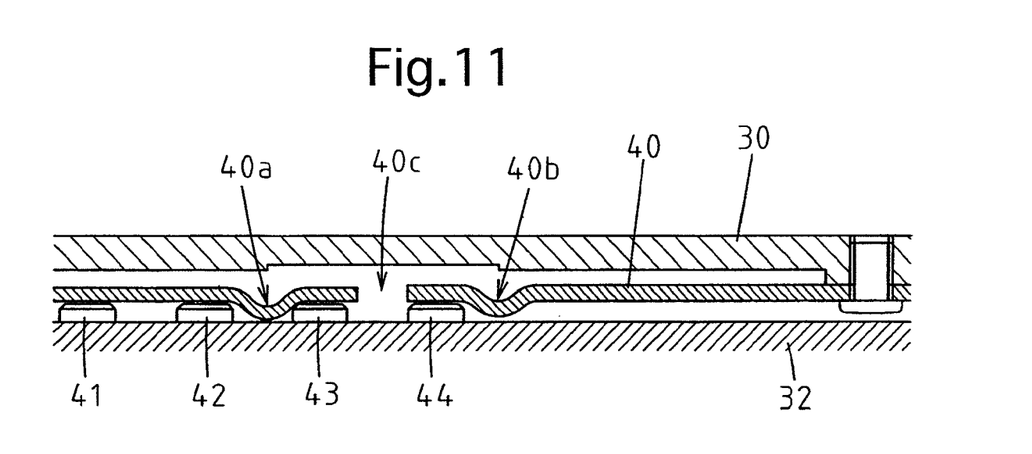

From this state, if the U-D bent state holding knob 7UD is operated to rotate in a rotation direction to bring the U-D bent state holding mechanism into the bent-state holding state (leftward with respect to FIG. 8), firstly the first click protrusion 41 causes the first protrusion 40a to abut against and subsequently ride over the first click protrusion 41 (i.e., the first click protrusion 41 slides under the first protrusion 40a) with a click action while resiliently deforming one leaf portion (first leaf portion) of the click leaf spring 40 which includes the first protrusion 40a, and simultaneously the third click protrusion 43 causes the second protrusion 40b to abut against and subsequently ride over the third click protrusion 43 (i.e., the third click protrusion 43 slides under the third click protrusion 43) with a click action while resiliently deforming the other leaf portion (second leaf portion) of the click leaf spring 40 which includes the second protrusion 40b, as shown in FIG. 9.

Thereafter, the first protrusion 40a slides into the gap between the first click projection 41 and the second click projection 42 while the second protrusion 40b slides into the gap between the third click projection 43 and the fourth click projection 44, so that the click leaf spring 40 returns to its original state (free state).

Consequently, at this stopped position, the U-D bent state holding knob 7UD enters a click-stopped state in which a tactile "click" is felt during the rotating operation of the U-D bent state holding knob 7UD so that the operator of the endoscope can feel a change in state of the U-D bent state holding knob 7UD with his/her hand. In this state, the U-D bent state holding knob 7UD is in the middle position within the range of rotation thereof, and a light frictional resistance is exerted on the rotating operation of the U-D control knob 5UD.

Thereupon, if the U-D bent state holding knob 7UD is further operated to rotate to the limit of rotation in the same rotation direction to bring the U-D bent state holding mechanism into the bent-state holding state, the second click protrusion 42 causes the first protrusion 40a to abut against and subsequently ride over the second click protrusion 42 with a click action while resiliently deforming the aforementioned first leaf portion of the click leaf spring 40, which includes the first protrusion 40a, the fourth click protrusion 44 causes the second protrusion 40b to abut against and subsequently ride over the fourth click protrusion 44 with a click action while resiliently deforming the aforementioned second leaf portion of the click leaf spring 40, which includes the second protrusion 40b, and simultaneously, the first protrusion 40a slides into the gap between the second click projection 42 and the third click projection 43 while the second protrusion 40b slides off the fourth click protrusion 44 so that the fourth click protrusion 44 is positioned immediately on the left side of the second protrusion 40b.

Consequently, at this stopped position, the U-D bent state holding knob 7UD enters a click-stopped state (second click-stopped state subsequent to the aforementioned click-stopped state) in which a tactile "click" is felt during the rotating operation of the U-D bent state holding knob 7UD so that the operator of the endoscope can again feel a change in state of the U-D bent state holding knob 7UD with the hand. In this state, the U-D bent state holding knob 7UD is in the bent-state holding state and a frictional resistance which is sufficiently great to keep the U-D control knob 5UD from rotating is exerted on the U-D control knob 5UD.

From this state, if the U-D bent state holding knob 7UD is operated to rotate in the reverse rotation direction to bring the U-D bent state holding mechanism into the bendable-portion free state, a tactile "click" is felt during the rotating operation of the U-D bent state holding knob 7UD so that the operator of the endoscope can again feel a change in state of the U-D bent state holding knob 7UD with the hand at two instances, i.e., upon the U-D bent state holding knob 7UD moving to the middle position in the range of rotation thereof and upon the U-D bent state holding knob 7UD moving to the limit of rotation thereof in the rotation direction to bring the U-D bent state holding mechanism into the bendable-portion free state, similar to the above described case where the U-D bent state holding knob 7UD is operated to rotate in the reverse rotation direction to bring the U-D bent state holding mechanism into the bent-state holding state.

In this manner, a click mechanism which provides a tactile "click" feel to the rotating operation of the U-D bent state holding knob 7UD is constructed of only the following two kinds of members: the click leaf spring 40, which is positioned so that the direction of thickness thereof corresponds to the direction of the axis of rotation of the U-D bent state holding knob 7UD (i.e., to the direction of the axis of rotation of the U-D control knob 5UD), and the four click projections 41 through 44, which are formed to project toward a surface of the click leaf spring 40. This configuration makes it possible to slim (reduce in size) the bent state holding mechanism so that the bent state holding mechanism can be installed in an internal space of the U-D control knob 5UD.

Accordingly, the operability of the endoscope can be improved by the miniaturization of the U-D control knob 5UD, and the aforementioned torque limiting mechanism (composed of the grooved rotational plate 17, the spring 25, the engaging arm 18, the engaging groove 21 and the engaging lug 22) or the like can be installed in an internal space of the U-D control knob 5UD with no need to increase the size of the U-D control knob 5UD.

Figure 12:
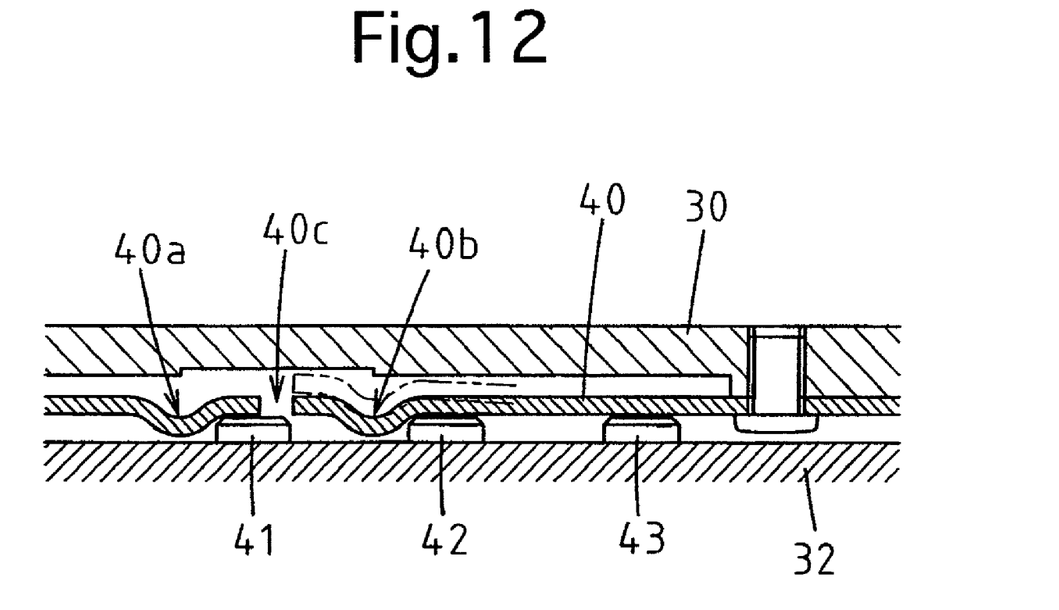
FIG. 12 is a schematic developed cross sectional view of a click leaf spring, click projections and associated members of another embodiment of the endoscope according to the present invention.

The present invention is not limited solely to the particular embodiment described above. For instance, an effect similar to that obtained in the above described embodiment can be obtained with the click leaf spring 40 and only the three click projections 41 through 43 if the click leaf spring 40 and the three click projections 41 through 43 are arranged so that only one of the three click projections 41 through 43 can be positioned between the first protrusion 40a and the second protrusion 40b at a time as shown in FIG. 12.

Although a sufficient click-stop holding force can be obtained with the click leaf spring 40, which is small in thickness and thereby makes it possible to contribute to miniaturization of the endoscope in the above described embodiment, it is possible that the click leaf spring 40 be provided with only one protrusion 40a or 40b if the click leaf spring 40 is made thicker.

Although there are two click-stopped settings in the range of rotation of the U-D bent state holding knob 7UD in the above described embodiments, only one click-stopped setting or more than two click-stopped settings can be provided in the range of rotation of the U-D bent state holding knob 7UD.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A bent state holding mechanism of an endoscope including a bender which has a rotatable bender to bend a bendable portion of an insertion portion of said endoscope, comprising:
a bent state holder to switch between a bent-state holding state, in which a frictional resistance is exerted on said bender to hold said bendable portion in a current position, and a bendable-portion free state, in which no frictional resistance is exerted on said bender, and
a clicker to provide a tactile feel to said rotating operation of said bent state holder at least one of when said bent state holder moves to said bent-state holding state and when said bent state holder moves to said bendable-portion free state,
wherein said clicker includes a click leaf spring formed so that a direction of thickness thereof corresponds to a direction of an axis of rotation of said bent state holder and shaped into an arc-shaped ring with a center thereof on said axis of rotation of said bent state holder, at least one protrusion being formed in said click leaf spring in said direction of thickness of said click leaf spring; and at least one click projection which projects toward a surface of said click leaf spring, one of said click leaf spring and said click projection being configured to rotate together with said bent state holder upon rotation thereof and the other thereof being fixed so that relative movement between said click leaf spring and said click projection can occur, and
wherein rotating said bent state holder causes said click projection to abut against said protrusion and thereafter ride over said protrusion with a click action while resiliently deforming said click leaf spring,
wherein said click leaf spring is formed as a substantially C-shaped ring, said protrusion of said click leaf spring being made in a vicinity of an opening of said C-shaped click leaf spring,
wherein a middle portion of said C-shaped click leaf spring in a circumferential direction thereof is fixed relative to a control portion so that portions of said C-shaped click leaf spring on opposite sides of said middle portion can be resiliently deformed independently of each other in said direction of thickness of said click leaf spring, and
wherein said middle portion of said C-shaped click leaf spring in a circumferential direction thereof is fixed relative to said control portion by at least one set-screw, a head of which also serves as a stop pin for determining the range of rotation of said bent state holder relative to said control portion.

2. The bent state holding mechanism according to claim 1, wherein rotating said bent state holder causes said click projections to abut against said protrusions and subsequently ride over said protrusions simultaneously, respectively.

3. The bent state holding mechanism according to claim 2, wherein rotating said bent state holder causes each of said click projections to abut against an adjacent one of said protrusions and subsequently ride over said adjacent protrusion at different positions within the range of rotation of said bent state holder.

4. The bent state holding mechanism according to claim 1, wherein said axis of rotation of said bent state holder corresponds with an axis of rotation of said bender.

5. The bent state holding mechanism according to claim 1, wherein two of said protrusions are formed in a vicinity of circumferentially-opposed ends of said C-shaped click leaf spring, respectively.

6. The bent state holding mechanism according to claim 2, wherein said protrusions are arranged at equi-angular intervals in an arc shape to face said surface of said of click leaf spring.

* * * * *